US010729211B2

(12) United States Patent
Sobol et al.

(10) Patent No.: US 10,729,211 B2
(45) Date of Patent: Aug. 4, 2020

(54) WRISTBAND LOCKING MECHANISM, WRISTBAND, WEARABLE ELECTRONIC DEVICE AND METHOD OF SECURING AN ARTICLE TO A PERSON

(71) Applicant: CareBand Inc., Chicago, IL (US)

(72) Inventors: Adam G. Sobol, Dayton, OH (US); Jason R. Gebhardt, Buffalo Grove, IL (US)

(73) Assignee: CAREBAND INC., Chicago, IL (US)

( * ) Notice: Subject to any disclaimer, the term of this patent is extended or adjusted under 35 U.S.C. 154(b) by 0 days.

(21) Appl. No.: 16/379,216

(22) Filed: Apr. 9, 2019

(65) Prior Publication Data

US 2019/0320766 A1   Oct. 24, 2019

Related U.S. Application Data

(60) Provisional application No. 62/761,961, filed on Apr. 12, 2018.

(51) Int. Cl.
| A44C 5/20 | (2006.01) |
| A61B 5/11 | (2006.01) |
| A41D 20/00 | (2006.01) |
| A44C 5/14 | (2006.01) |
| A61B 5/00 | (2006.01) |

(52) U.S. Cl.
CPC ............ *A44C 5/2042* (2013.01); *A41D 20/00* (2013.01); *A44C 5/14* (2013.01); *A61B 5/1112* (2013.01); *A61B 5/681* (2013.01); *A61B 2503/08* (2013.01)

(58) Field of Classification Search
CPC ......... A44C 5/24; A44C 5/246; A44C 5/2052; A44C 5/14; Y10T 24/215; Y10T 24/4782; Y10T 24/2166; Y10T 24/45743; Y10T 24/45749; Y10T 24/45754
See application file for complete search history.

(56) References Cited

U.S. PATENT DOCUMENTS

| 4,928,359 | A | * | 5/1990 | Gagnebin | ............ | A44C 5/2042 24/587.11 |
| 5,485,659 | A | * | 1/1996 | Kashikie | ............... | A44C 5/2052 24/265 WS |
| 5,711,056 | A | * | 1/1998 | Taguchi | ............... | A44C 5/2052 24/265 WS |
| 5,787,554 | A | * | 8/1998 | Hashimoto | ............ | A44C 5/185 24/265 WS |
| 6,023,816 | A | * | 2/2000 | Okada | ...................... | A44C 5/24 24/265 WS |

(Continued)

*Primary Examiner* — Corey N Skurdal

(57) ABSTRACT

A wristband locking mechanism for a wearable electronic device, a wristband, a wearable electronic device and a method of securing an article to a person. The wristband locking mechanism includes a clasp assembly with independently-operable spring-biased actuators such that the wristband locking mechanism cannot be unlocked using one hand. The use of sensors, processors, communication equipment and associated components within the wearable electronic device allows a caregiver to monitor one or more of location, environmental, physiological and activity data of a wearer of the device, while the requirement for two-handed operation for unlocking of the wristband locking mechanism provides a deterrent against intentional or unintentional removal of the attached article or wearable electronic device by the wearer.

17 Claims, 14 Drawing Sheets

(56) References Cited

U.S. PATENT DOCUMENTS

| | | | |
|---|---|---|---|
| 7,412,755 B2* | 8/2008 | Tetu | A44C 5/24 24/265 WS |
| 8,935,834 B2* | 1/2015 | Mouche | A44C 5/24 224/164 |
| 9,198,485 B2* | 12/2015 | Kaltenrieder | A44C 5/14 |
| 9,986,796 B2* | 6/2018 | Catanese | A44C 5/24 |
| 2016/0037879 A1* | 2/2016 | Qian | A44B 11/258 24/3.2 |
| 2016/0081439 A1* | 3/2016 | Catanese | A44B 11/226 63/3.1 |
| 2017/0215531 A1* | 8/2017 | Wong | A44C 5/22 |
| 2019/0335862 A1* | 11/2019 | Raille | A44C 5/185 |

* cited by examiner

WRISTBAND LOCKING MECHANISM, WRISTBAND, WEARABLE ELECTRONIC DEVICE AND METHOD OF SECURING AN ARTICLE TO A PERSON

This application claims the benefit of U.S. Provisional Application Ser. No. 62/761,961 that was filed on Apr. 12, 2018.

The present disclosure relates to a wristband locking mechanism that requires two-handed operation for removal of the device from the wearer.

BACKGROUND

Dementia—such as Alzheimer's Disease, Parkinson's Disease and related neurodegenerative conditions—corresponds to a decline in mental ability severe enough to interfere with one's daily life, including the activities of daily living (ADL). Over five million people suffer from dementia in the United States alone, and this number is predicted to increase.

One problem in caring for those suffering from dementia is that they may become confused of their surroundings and tend to wander and get lost. If these individuals are not located in a timely manner, they are at risk of injury. To compound the problem, many of the individuals suffering from dementia will not have the mental acuity to remember their name, place of residence or other identifying indicia even in the event they encounter someone trying to assist them. Another problem in caring for those suffering from dementia is that their decline is often accompanied by corresponding declines in mental or physical health, particularly in the elderly. For example, individuals suffering from dementia may be prone to infections, pneumonia, neuropsychiatric symptoms or other comorbidities.

The problem associated with caring for an individual with such mental and physical conditions is exacerbated in situations where the caregiver—whether a doctor, nurse, therapist, home care aide, family member, friend or the like—is not able to be with the individual at all times of the day and night in order to acquire one or more of location, environmental, physiological and activity information that might otherwise provide an indication that the individual is symptomatic, in danger of wandering, in an unsafe environment or the like. Moreover, caring for individuals that are suffering from either or both of mental and physical frailties is particularly acute in group settings such as nursing homes, assisted living communities or related long-term health care centers, where the ability to ascertain in a timely manner the location or activity of a person residing within is hampered by the large number of people requiring such care relative to the number of caregivers.

Location-tracking devices may be used with people that may have a propensity for wandering, such as those suffering from Alzheimer's Disease, dementia or other cognitive frailties. Securing such a location-tracking device to a person may be accomplished with conventional wristbands, ankle bracelets, pendants or the like. Unfortunately, the person's cognitive impairment and associated confusion may lead to attempts by the person to remove the device in such a way as to render it ineffective for its intended purpose. Accordingly, conventional securing mechanisms such as those associated with wristwatches, jewelry or the like that are designed to be easily removed by the wearer without the need for additional assistance are unsuitable for persons that are afflicted with cognitive impairment and wearing such a location-tracking device.

SUMMARY

In view of these problems, the wristband locking mechanism and methods of the present disclosure permit caregivers to ensure that once the mechanism is secured to the wearer, the wearer will require assistance in order to subsequently remove it. For example, in a situation where a wearable electronic device (also referred to herein as a wellness-monitoring device) such as that used to track one or more of the location, environmental, physiological and activity data of an individual is configured to be wrist-wearable, the use of two distinct and independently-operated spring-biased actuators that are part of a clasp assembly within the wristband locking mechanism is such that two-handed operation is required to unlock the device, which in turn helps ensure that the wearer does not inadvertently or intentionally remove the device.

According to one embodiment of the present disclosure, a wristband locking mechanism includes a housing assembly and a clasp assembly cooperative with the housing assembly. The clasp assembly includes one or more lock arms, a first spring-biased actuator and a second spring-biased actuator. The first spring-biased actuator is coupled to the one or more lock arms to provide a first selective interference fit between the one or more lock arms and a portion of the housing assembly, while the second spring-biased actuator is coupled to the one or more lock arms to provide a second selective interference fit between the one or more lock arms and another portion of the housing assembly. In operation, when the first and second spring-based actuators are simultaneously engaged by a user independent of one another (that is to say, with one being actuated by a first hand and a second being actuated by another hand), a state (such as from a locked position to an unlocked position or from an unlocked position to a locked position) of the wristband locking mechanism is changed.

According to another embodiment of the present disclosure, a wristband is disclosed. The wristband includes an elongate strap and a housing assembly, where the two are secured such that the housing assembly that makes up a part of a wristband locking mechanism further includes a clasp assembly. The clasp assembly includes one or more lock arms, as well as first and second spring-biased actuators. The first spring-biased actuator is cooperative with the one or more lock arms to provide a first selective interference fit between the one or more lock arms and a portion of the housing assembly. The second spring-biased actuator is cooperative with the one or more lock arms to provide a second selective interference fit between the one or more lock arms and a portion of the housing assembly. The state of locking of the wristband locking mechanism changes upon the first and second spring-based actuators being simultaneously engaged through two-handed user actuation.

According to yet another embodiment of the present disclosure, a wearable electronic device is disclosed. The wearable electronic device includes a person tracking mechanism and a wristband where the latter includes a locking mechanism and an elongate strap at least one of which is secured to the person tracking mechanism. The locking mechanism includes a housing assembly and a clasp assembly. The clasp assembly includes one or more lock arms and first and second spring-based actuators. The first spring-biased actuator is cooperative with the one or more lock arms to provide a first selective interference fit between the one or more lock arms and a portion of the housing assembly, while the second spring-biased actuator is cooperative with the one or more lock arms to provide a second selective interference fit between the one or more lock arms and a portion of the housing assembly. The state of locking of the locking mechanism changes upon the first and second spring-based actuators being simultaneously engaged through two-handed user actuation. In one non-limiting form, the person tracking mechanism includes one or more sensors, a wireless communication module and a processor coupled to a non-transitory computer readable medium having executable instructions thereon. In such a form, the sensors detect one or more of environmental data, activity data and physiological data from a person that is wearing the device or to whom the device is otherwise secured, while the wireless communication module can selectively receive location data through various signals. In one form, such signals include those from near-range, private-network infrastructure (that is to say, those that do not require cellular or related public-network features in order to send and receive wireless signals) such as a local area network (LAN) or a personal area network (PAN) in general and a Bluetooth Low Energy (BLE) network in particular for indoor operation. In addition, such signals may include those from a global navigation satellite system (GNSS) in order to satisfy outer, long-range location needs. Within the present disclosure, GNSS is the standard generic term for satellite navigation systems that provide autonomous geo-spatial positioning with global coverage and is meant to includes specific embodiments such as global positioning system (GPS), the Russian global navigation satellite system (GLONASS), Galileo, Beidou and other regional systems. The communication module also selectively transmits one or more of the sensed location data, environmental data, activity data and physiological data using a low power wide area network (LPWAN) signal. As such, within the present context, the wireless communication module includes the ability to receive both a GNSS signal and a BLE signal, as well as the ability to transmit an LPWAN signal (in general) and a LoRaWAN signal (in particular). The processor responds to executable instructions that are stored in the non-transitory computer readable medium that acts as a memory, thereby permitting the sensor or sensors to acquire the various forms of data for which they are designed, as well as to permit the wireless communication module to receive and transmit various forms of the received location, environmental, activity and physiological data.

According to still another embodiment of the present disclosure, a method of securing a wearable electronic device to a person is disclosed. The method includes forming a wristband by securing a locking mechanism and a wearable electronic device to an elongate strap, attaching the wristband to a wrist of the person and locking the locking mechanism. The wristband locking mechanism includes features such as those discussed in the previous embodiments such that the wristband locking mechanism can be unlocked and removed by anyone using a two-hand grip, while preventing the unlocking and subsequent removal by the wearer or anyone else using only one hand.

BRIEF DESCRIPTION OF THE SEVERAL VIEWS OF THE DRAWINGS

The following detailed description of specific embodiments of the present disclosure can be best understood when read in conjunction with the following drawings, where like structure is indicated with like reference numerals and in which.

DETAILED DESCRIPTION

The disclosed devices and methods include a wristband locking mechanism, wristband and wearable electronic device the latter of which can provide real-time location tracking and data informed care insights through the analysis of person movements and other activity for indicators of potential health complications. The locking mechanism, as well as the wristband and wearable electronic device to which the locking mechanism is attached, includes features to deter a patient or other person who is wearing the wristband, wearable electronic device or both from unlocking and removing them. By its construction, the wristband locking mechanism requires the use of simultaneous two-handed operation that inhibits the wearer from unaccompanied wristband or wearable electronic device removal, as well as in situations involving an attempted removal by the wearer when accompanied by another who may be afflicted with dementia, Alzheimer's Disease or other cognitive disorders.

Figure 1A:
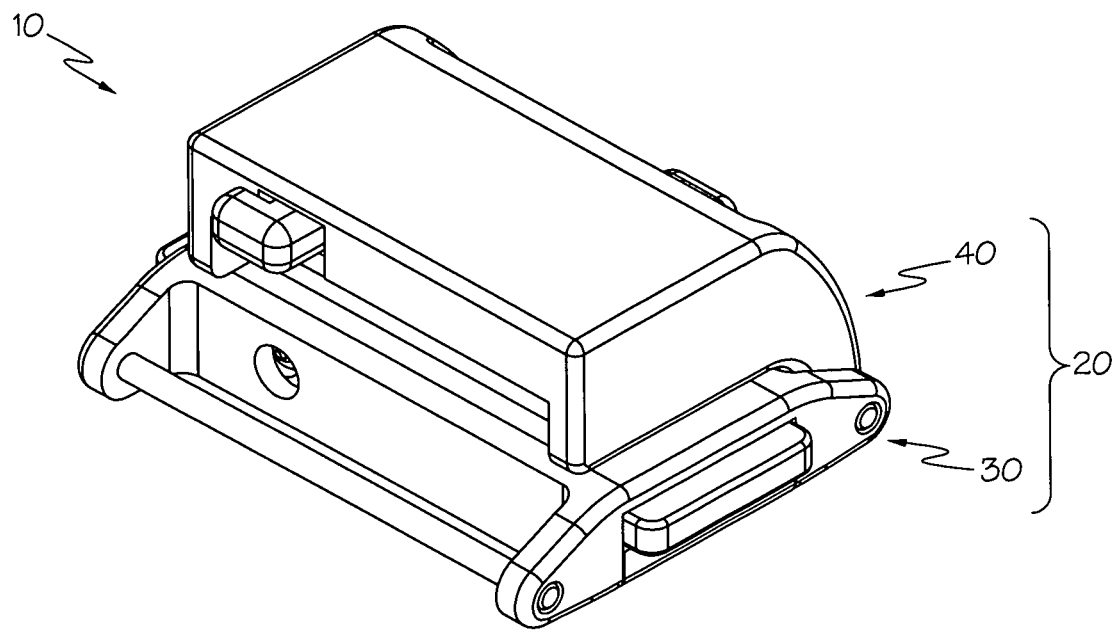
FIG. 1A depicts an upper perspective view of an as-assembled wristband locking mechanism in a locked position according to one or more embodiments shown or described herein.
Figure 1B:
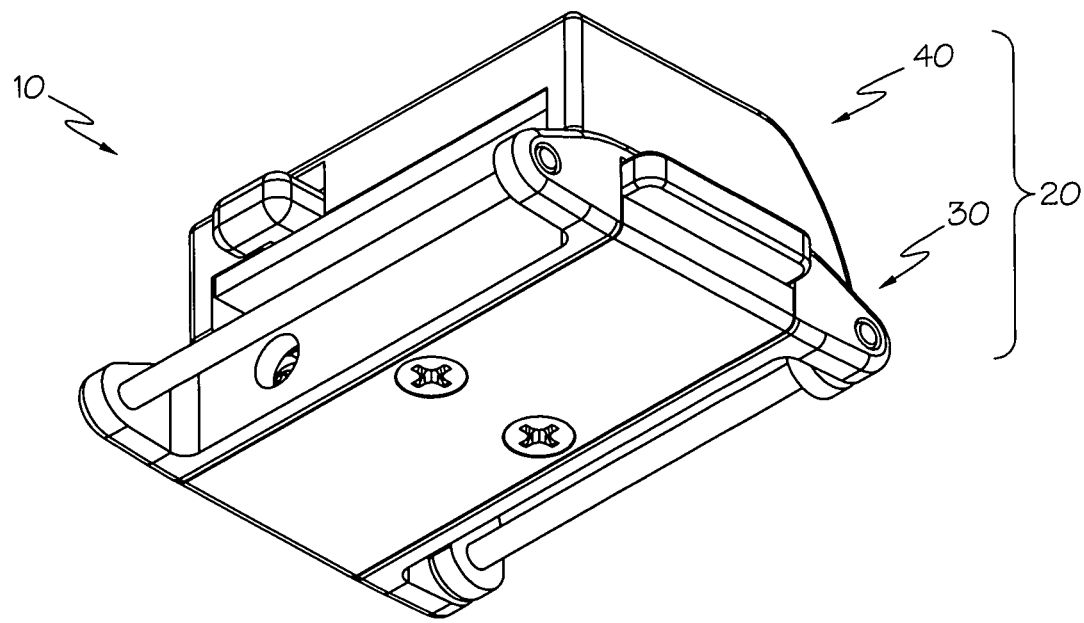
FIG. 1B depicts a lower perspective view of the wristband locking mechanism of FIG. 1A.
Figure 7A:
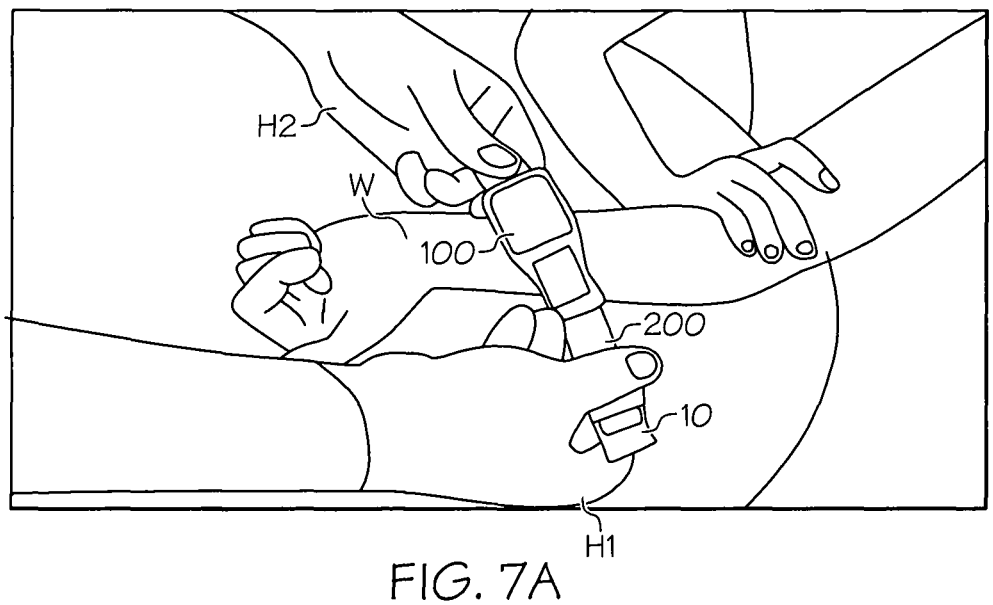
FIG. 7A depicts one notional step in a sequence of steps used to secure a wearable electronic device to a person according to one or more embodiments shown or described herein.
Figure 7B:
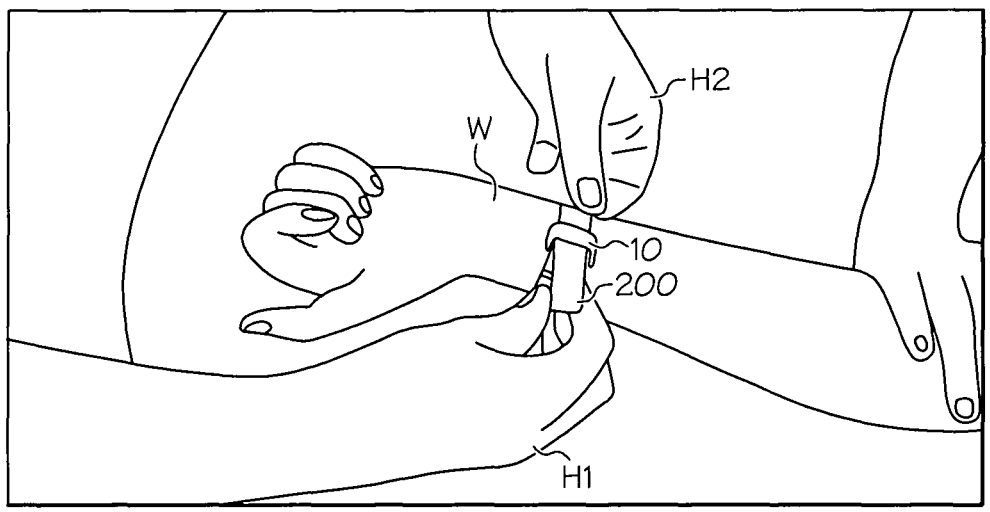
FIG. 7B depicts a subsequent notional step in a sequence of steps used to secure a wearable electronic device to a person according to one or more embodiments shown or described herein.

Referring first to FIGS. 1A through 1D, various views of the external features of a wristband locking mechanism 10 according to the present disclosure are shown. Referring with particularity to FIGS. 1A and 1B, in one form, the wristband locking mechanism 10 includes a housing assembly 20 made up of a lower housing assembly 30 and an upper housing assembly 40. Within the present disclosure, it is to be understood that the term "wristband locking mechanism" is meant to describe the wristband locking mechanism 10 independent from any wristband to which it may be connected, attached, affixed or otherwise secured and that if such connectivity is intended, the context will so indicate. Also within the present disclosure, it will be understood that the terms "lower" and "upper" used to describe the corresponding housing assemblies 30, 40 are reference-frame dependent, and that the description of such housing assemblies 30, 40 will be apparent from the context. Nevertheless, for convenience, the lower housing assembly 30 as discussed herein is the one that is affixed to a wristband (such as that which is depicted in FIG. 5C), or that is disposed closer to the wrist of a user (such as that which is depicted in FIGS. 7A and 7B). In either event, in a general sense, it is the upper housing assembly 40 that moves in response to an unlocking operation, while it is the lower housing assembly 30 that remains generally stationary in response to such unlocking operation.

Figure 1C:
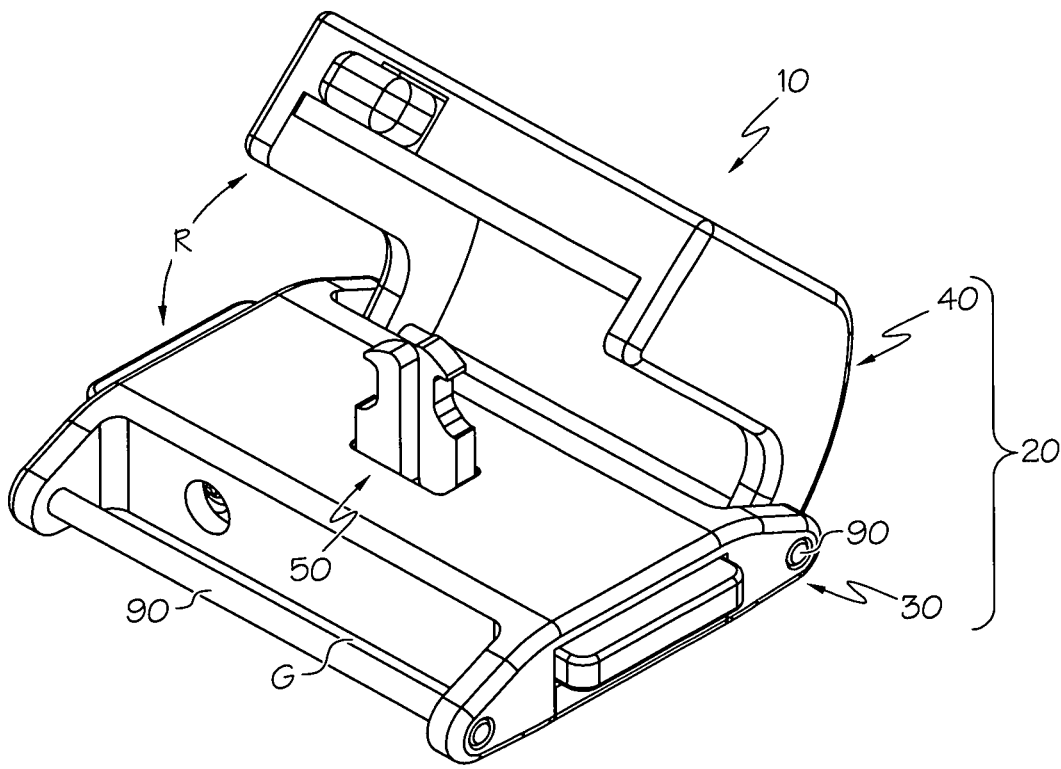
FIG. 1C depicts the wristband locking mechanism of FIG. 1A in an unlocked position.
Figure 1D:
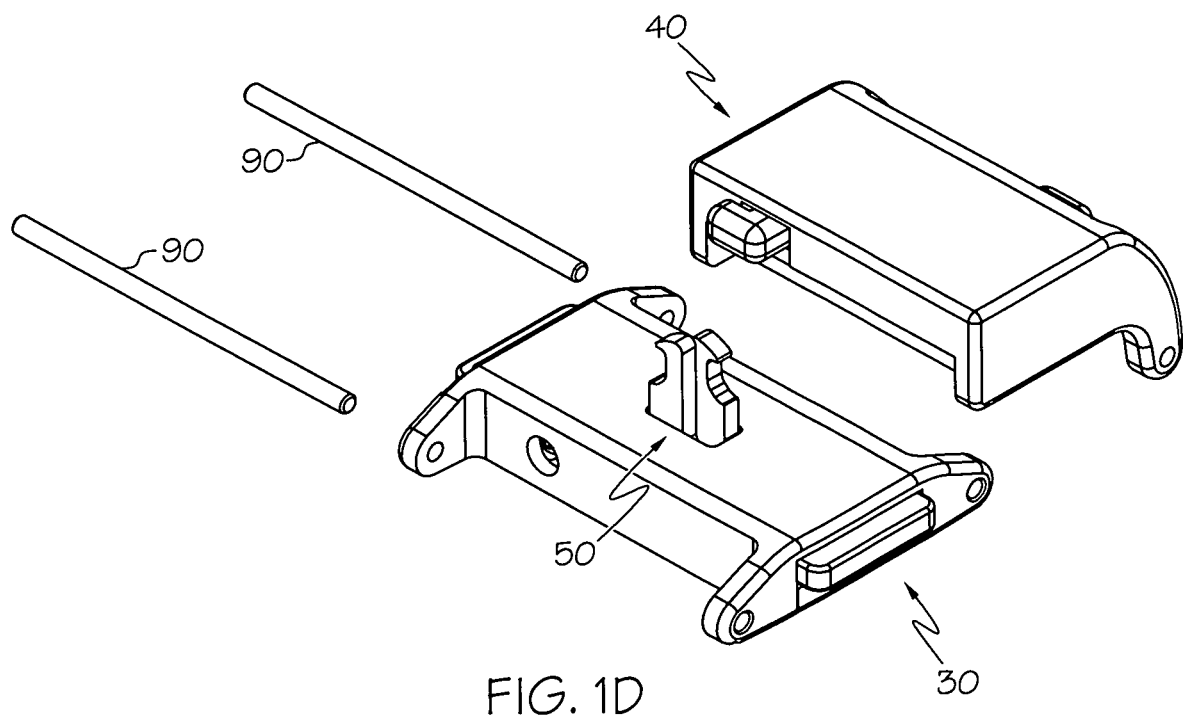
FIG. 1D depicts a partial upper exploded view of the wristband locking mechanism of FIG. 1A.

Referring with particularity to FIGS. 1C and 1D, in one form, the upper housing assembly 40 is hingedly connected to the lower housing assembly 30 through one of two dowel pins 90 such that the upper housing assembly 40 may rotate R about the elongate axis of the dowel pin 90. As can be seen, both the dowel pin 90 that is used to create the hinged connection, as well as the one on the opposite side of the lower housing assembly 30, are spaced from the lower housing assembly 30 to create a gap G that allows the passage of an elongate strap (such as that depicted in FIG. 6) that can function as a wristband. The lower housing 30 may also contain a portion of the clasp assembly 50 that performs the locking and unlocking functions of the wristband locking mechanism 10.

Referring next to FIGS. 2A through 2F, details of both the lower housing assembly 30 and a portion of the clasp assembly 50 are shown. In particular, various views of some of the individual components that make up the clasp assembly 50, as well as their placement in relation to an enclosure that is formed by the lower housing assembly 30, depict the mechanical cooperation between the lower housing assembly 30 and the clasp assembly 50 needed to promote the locking and unlocking of the wristband locking mechanism 10.

Figure 2A:
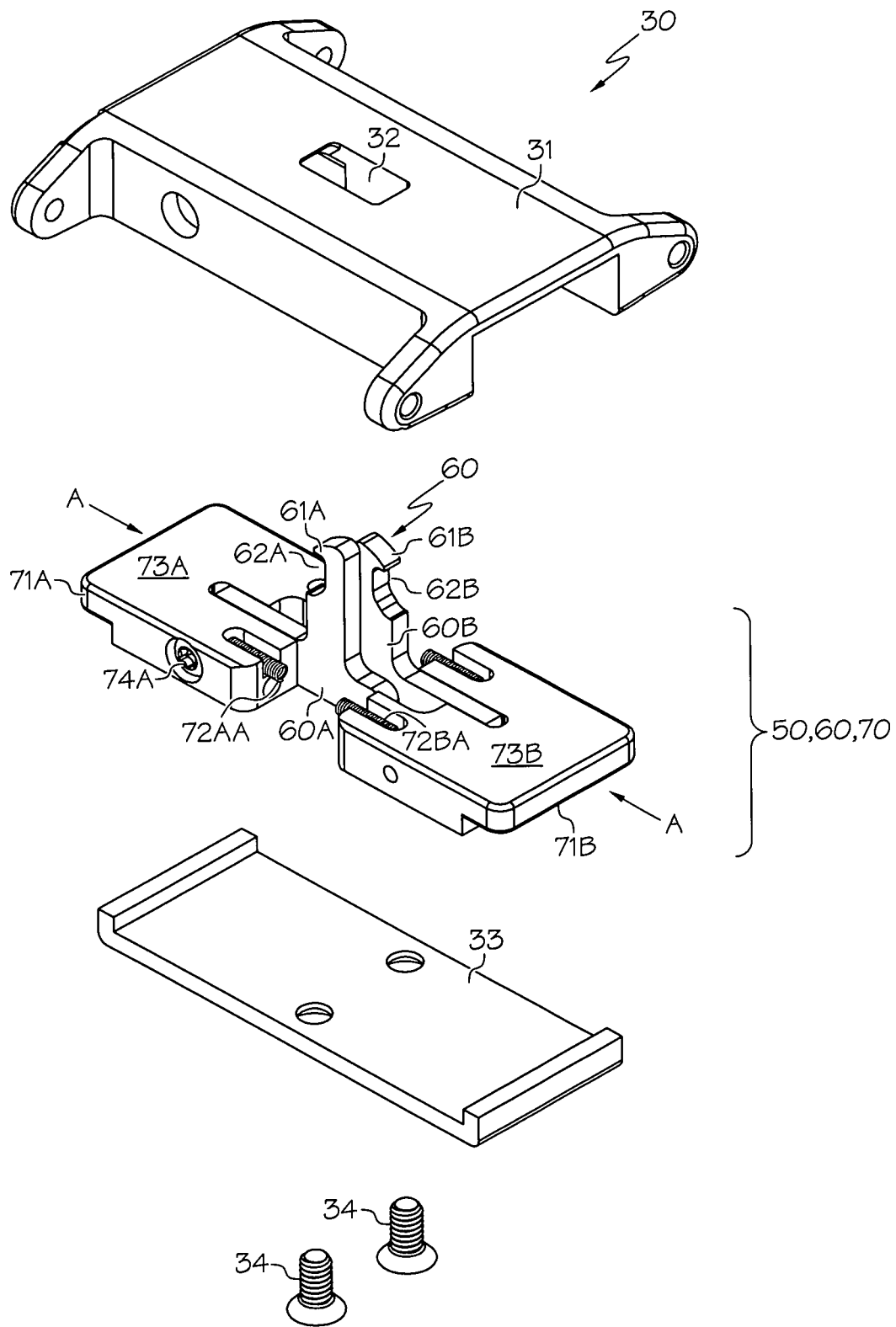
FIG. 2A depicts an upper exploded view of a lower housing assembly of the wristband locking mechanism of FIG. 1A.
Figure 2B:
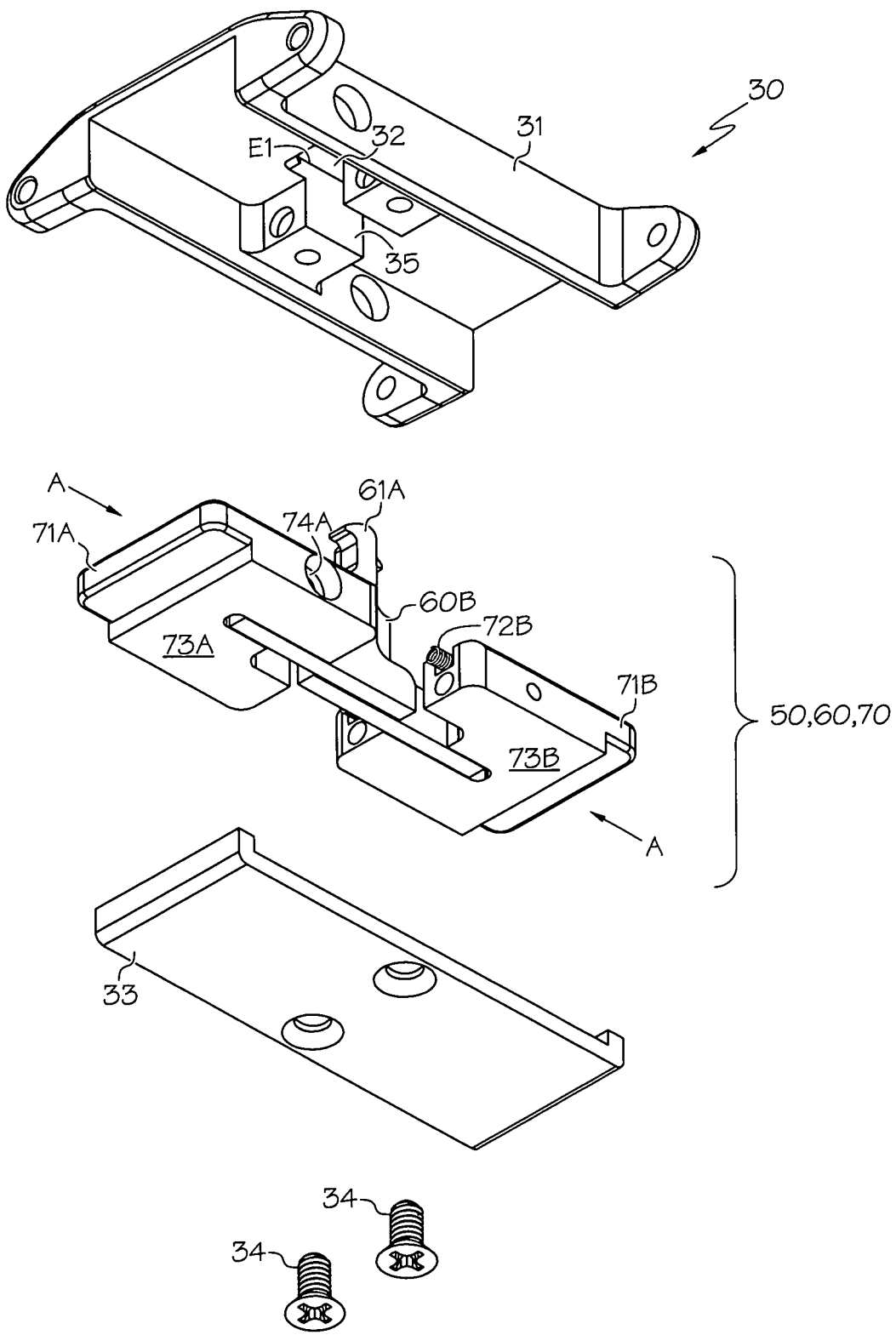
FIG. 2B depicts a lower exploded view of the lower housing assembly of FIG. 2A.

Referring with particularity to FIGS. 2A and 2B, the exploded views show that in addition to a generally rectangular-shaped cover 31 that defines a generally rectangular-shaped aperture 32 in an upper surface thereof, the lower housing assembly 30 includes a base (shown presently in the form of a plate) 33, as well as fasteners 34 to secure the cover 31 and base 33 together to contain at least some of the components that make up the clasp assembly 50. The clasp assembly 50 includes a lock arm pair 60 made up of individual lock arms 60A, 60B, as well as a first spring-biased actuator 70 and a second spring-biased actuator 80 the latter of which will be discussed in conjunction with FIGS. 3A through 3D. Each of the lock arms 60A, 60B include respectively both a hook-shaped distal tip 61A, 61B and an undercut region 62A, 62B immediately below the corresponding distal tip 61A, 61B; it is these end features of the lock arms 60A, 60B that will help define an interference fit I that will be discussed in more detail in conjunction with FIGS. 4A through 4C. Within the present context, the individual lock arms 60A, 60B of the lock arm pair 60—while capable of being independently moveable relative to one another—are designed to help the clasp assembly 50 achieve its unlocking function when both are moved simultaneously in opposing directions along the actuation axis (also referred to herein as common axial dimension) A. The first spring-biased actuator 70 includes opposing release buttons 71A, 71B, numerous springs 72A, 72B, platforms 73A, 73B and corresponding fasteners 74A, 74B. In one form, the platforms 73A, 73B are used to provide a rigid coupling between the release buttons 71A, 71B and their respective lock arms 60A, 60B, as well as a mounting location for the release buttons 71A, 71B, springs 72A, 72B and fasteners 74A, 74B to allow the corresponding release buttons 71A, 71B and platforms 73A, 73B to cooperate with one another in order to overcome the bias of the springs 72A, 72B to allow lock arm 60A, 60B movement along the actuator dimension A. In one form, the release buttons 71A, 71B and their respective platforms 73A, 73B can be joined together or otherwise made into a single, unitary structure, such as through a casting or related forming process. In one form, duplicate ones of the individual components that make up the lock arm pair 60 and the first spring-biased actuator 70 may be identical in structure or construction to one another. For example, lock arm 60A may be made from an identical mold as lock arm 60B, as can release buttons 71A and 71B and their respective platforms 73A and 73B, springs 72A and 72B and fasteners 74A and 74B. Such common construction or formation can reduce inventory part count, as well as reduce the complexity of tooling or other fabrication equipment used to make the various individual components.

While it would be possible to employ a single lock arm with which to achieve the interference fit I and corresponding locking relationship between the lower housing assembly 30 and the upper housing assembly 40, the authors of the present disclosure are of the belief that using two individual lock arms 60A, 60B and corresponding release buttons 71A, 71B as part of the first spring-biased actuator 70 is preferable. By employing two spaced-apart release buttons 71A, 71B in conjunction with the independent unlocking operations of two spaced-apart release buttons 81A, 81B of the second spring-biased actuator 80 that will be discussed in more detail in conjunction with FIGS. 3A through 3D, single-handed unlocking operation is inhibited, which in turn makes it more difficult for a wearer of a corresponding wristband or wearable electronic device to remove it by himself or herself.

Figure 2C:
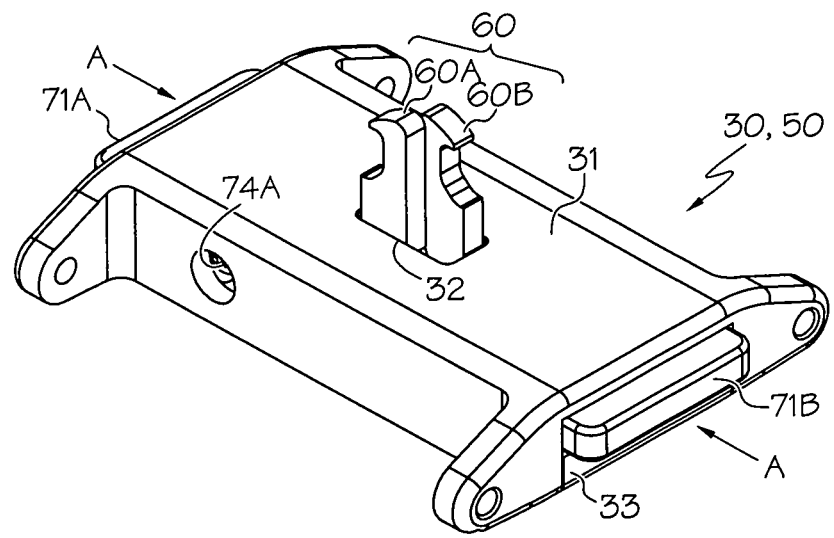
FIG. 2C depicts an upper perspective view of the lower housing assembly of the wristband locking mechanism of FIG. 1A.
Figure 2D:
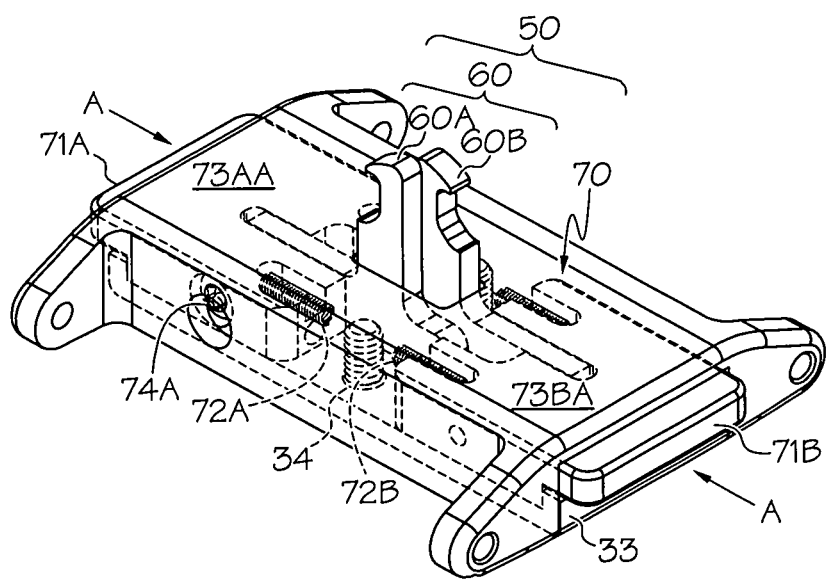
FIG. 2D depicts the lower housing assembly of FIG. 2C with partial shading to show various internal components.

Referring with particularity to FIGS. 2C and 2D, the as-assembled and partially-transparent views of the lower housing assembly 30 and a remaining portion of the clasp assembly 50 show that size and shape of the aperture 32 that is formed in cover 31 is such that it acts as a stop for outward movement of the lock arm pair 60 along the actuation axis A, thereby defining a maximum travel path along such axis not just for the lock arms 60A, 60B themselves, but also the rigidly-affixed release buttons 71A, 71B of the first spring-biased actuator 70. Moreover, by maintaining the dimensions of the aperture 32 relatively close to those defined by the cross-sectional area of the lock arm pair 60 within the plane of the cover 31, the chance of dust, dirt and other contaminants getting into a volumetric region defined by the cover 31 and base 33 is reduced.

Figure 2E:
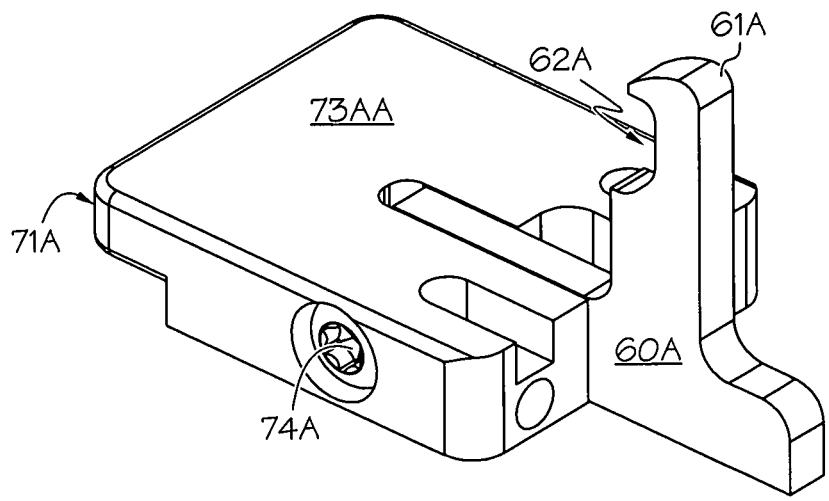
FIG. 2E depicts an upper perspective view of a release button and hook arm assembly of the lower housing assembly of FIG. 2A.
Figure 2F:
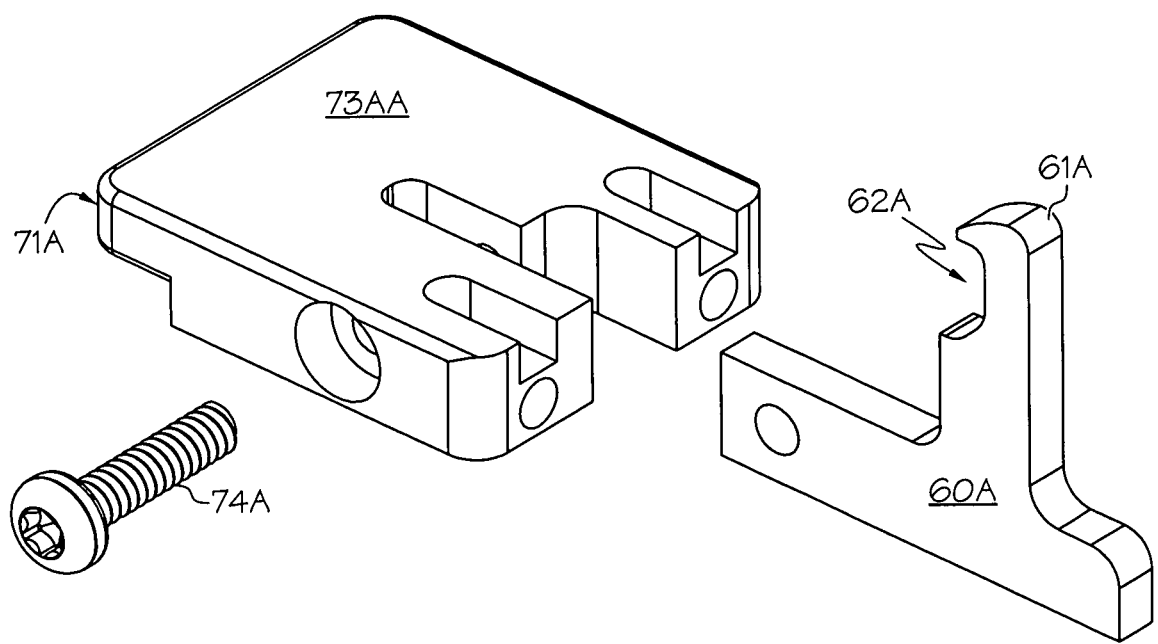
FIG. 2F depicts an upper exploded view of the release button and hook arm assembly of FIG. 2E.

Referring with particularity to FIGS. 2E and 2F, details of one of the lock arm pair 60 (in particular lock arm 60A) respective platform 73A and fastener 74A are shown in an assembled (FIG. 2E) and disassembled (FIG. 2F) state. In one form, these various components may be made with rigid, structural materials including metals or certain plastics, depending on the structural, durability or other application-specific need.

Referring next to FIGS. 3A through 3D, details of the upper housing assembly 40 and the second spring-biased actuator 80 that makes up the remainder of clasp assembly 50 are shown. A cover 41 and base 42 cooperate to define a generally rectangular-shaped enclosure for the containment of at least some of the components that make up the second spring-biased actuator 80. In addition to providing a mounting surface upon which the second spring-biased actuator 80 may be placed and secured, the base 42 further defines a generally rectangular-shaped aperture 43 in its generally planar surface. The aperture 43 is sized and shaped to promote the selective interference fit I of FIGS. 4A through 4C between it and the hook-shaped distal tips 61A, 61B of the lock arms 60A, 60B. Fasteners 44 are used to secure the cover 41 and base 42 together, while a hinged arm that extends downwardly from the cover 41 may be used as part of a hinged connection with one of the dowel pins 90 of FIGS. 1A through 1D.

Figure 3A:
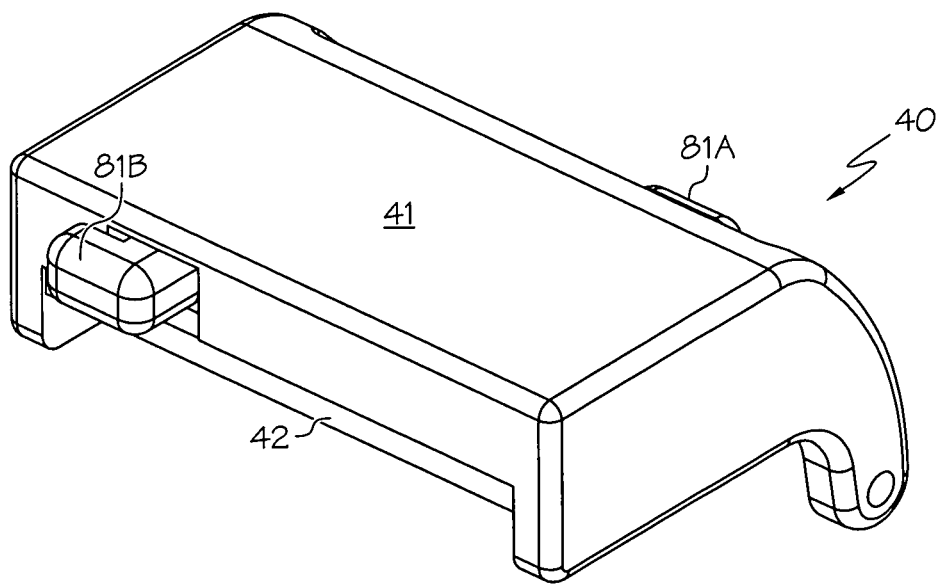
FIG. 3A depicts an upper perspective view of an upper housing assembly of the wristband locking mechanism of FIG. 1A.
Figure 3B:
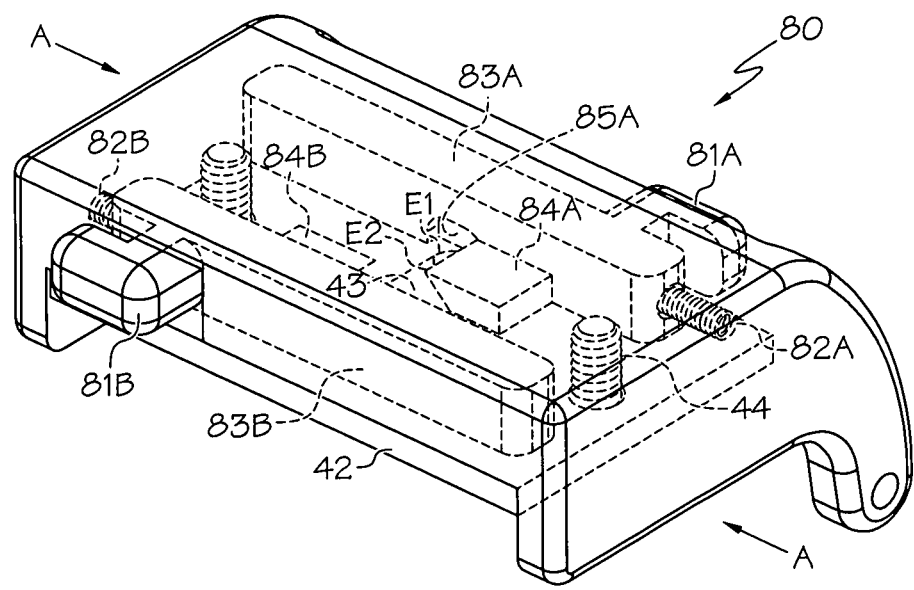
FIG. 3B depicts the upper housing assembly of FIG. 3A with partial shading to show various internal components.
Figure 3C:
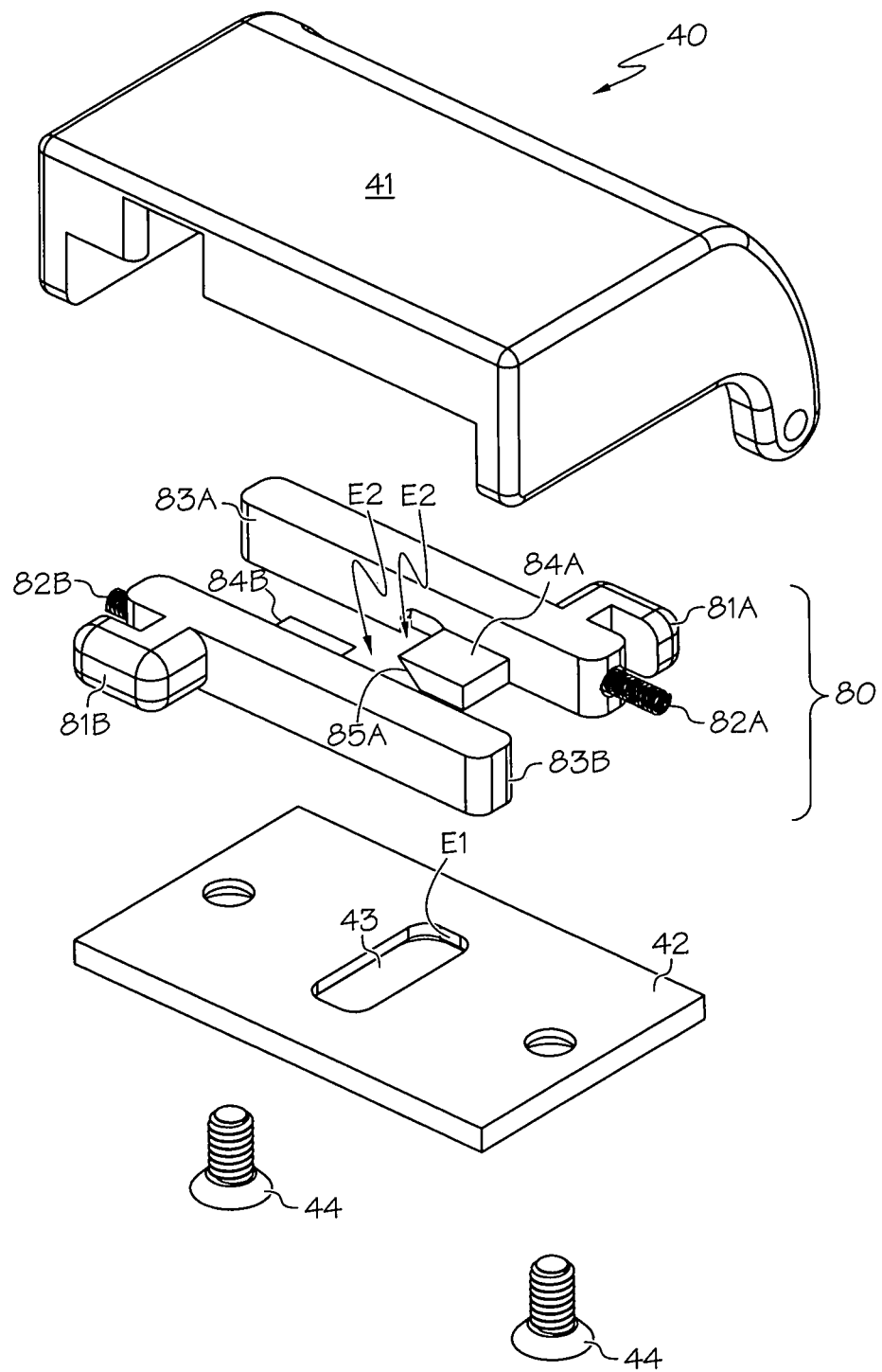
FIG. 3C depicts an upper exploded view of the upper housing assembly of FIG. 3A.
Figure 3D:
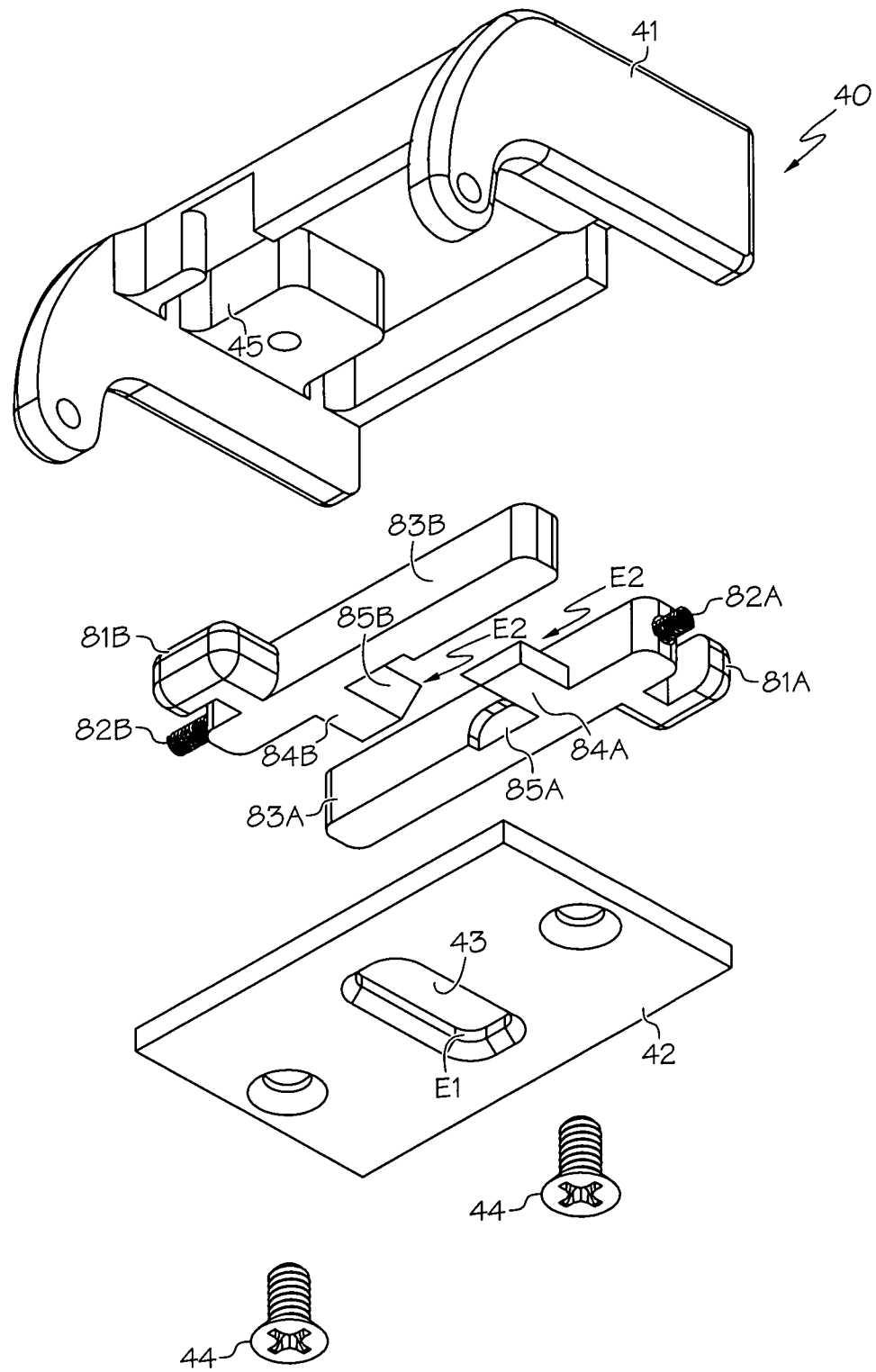
FIG. 3D depicts a lower exploded view of the upper housing assembly of FIG. 3A.

Referring with particularity to FIG. 3A, the upper housing assembly 40 is shown in its as-assembled form where a majority of the components making up the second spring-biased actuator 80 are contained within the enclosure that is defined by the cover 41 and base 42. Referring with particularity to FIGS. 3B through 3D, the exploded and partially-transparent views allow the internal features of the second spring-biased actuator 80, as well as the placement of—and mechanical cooperation between—its individual components and the upper housing assembly 40 needed to promote the locking and unlocking of the wristband locking mechanism 10 to be shown. In particular, components that make up the second spring-biased actuator 80 include opposing release buttons 81A, 81B, springs 82A, 82B, platforms 83A, 83B and sliders 84A, 84B. In one form, the platforms 83A, 83B are used to provide a rigid coupling between the release buttons 81A, 81B and their respective sliders 84A, 84B with corresponding inclined planes 85A, 85B, as well as a mounting location for the release buttons 81A, 81B and springs 82A, 82B. This in turn allows the corresponding release buttons 81A, 81B, platforms 83A, 83B and sliders 84A, 84B to cooperate with one another in order to overcome the bias of the springs 82A, 82B to permit the movement of the sliders 84A, 84B away from one another along the actuator dimension A. In one form, the release buttons 81A, 81B, platforms 83A, 83B and sliders 84A, 84B may be joined or formed to define a single, unitary structure in a manner generally similar to that of the release buttons 71A, 71B and their respective platforms 73A, 73B of the first spring-biased actuator 70. In one form, the release buttons 81A, 81B may include a generally L-shaped profile (as can be seen in FIGS. 3B and 3C) such that they can translate back-and-forth within a slot formed on an adjacent part of the cover 41 to allow movement necessary along the actuation axis A while keeping an opening formed by the slot relatively small in order to reduce the likelihood of dust, dirt and other contaminants from reached the enclosed region that is between the cover 41 and base 42. In one form, the duplicate ones of the individual components that make up the second spring-biased actuator 80 may be identical in structure or construction to one another in a manner generally similar to the previously-discussed components of the first spring-biased actuator 70.

Various edges $E_1$, $E_2$ may be formed respectively on the surface of the base 42 and sliders 84A, 84B. These edges $E_1$, $E_2$ are sized and shaped to ensure a location for selective contact between them and the undercut regions 62A, 62B of the distal tips 61A, 61B of the lock arms 60A, 60B, where such contact corresponds to the interference fit I of FIGS. 4A through 4C that maintains the clasp assembly 50 (and therefore, the locking mechanism 10) in a locked position. Within the present context, an edge that facilitates the selective interference fit between the hook-like distal tips 61A, 61B of the lock arms 60A, 60B can be any surface discontinuity that allows the distal tips 61A, 61B to contact the discontinuity in such a way that relative movement between the two is substantially inhibited until such time as the edge and a respective one of distal tips 61A, 61B of the lock arms 60A, 60B are moved out of one another's way such that freedom of movement along the actuation dimension A is established. Such edge may be formed as a stationary cutout (such as edge $E_1$ associated with the aperture 43 that is formed within the base 42 of the upper housing assembly 40), as well as part of a movable structure (such as the edges $E_2$ each of which are associated with the sliders 84A, 84B that are formed as part of the second spring-biased actuator 80). Within the present context, a part or component such as the sliders 84A, 84B is deemed to be moveable when its position within the locking mechanism 10 can be changed relative to one or both of the lower housing assembly 30 and upper housing assembly 40 as a result of the locking and unlocking operations that are discussed within the present disclosure. It will be appreciated that the shape of such an edge is not critical so long as it is capable of forming the selective interference fit between it and the lock arms 60A, 60B to a degree sufficient to inhibit the unlocking of the locking mechanism 10 without having first gone through the two-handed unlocking operation discussed herein. Referring with more particularity to FIG. 3D, one or more mounting blocks 45 may be integrally formed with the cover 41 to provide both partial confinement of lateral movement of the platforms 83A, 83B, but also to include a threaded aperture with which to accept the fasteners 44.

Figure 4A:
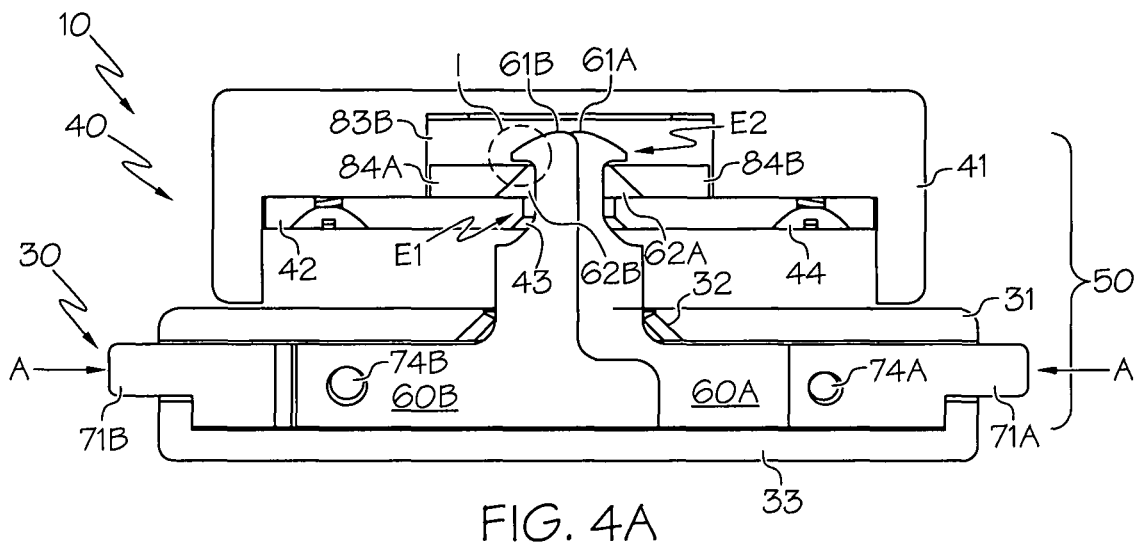
FIG. 4A depicts an elevation cutaway view of the position of the lock arms prior to an unlocking movement being imparted to either of the spring-biased actuators of the clasp assembly.
Figure 4B:
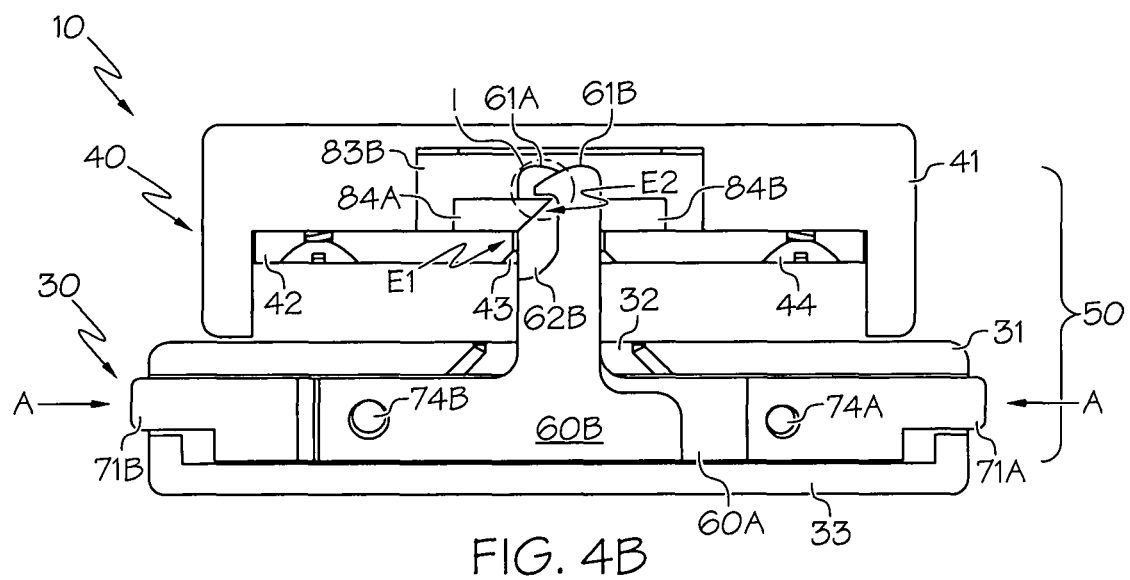
FIG. 4B depicts an elevation cutaway view of the position of the lock arms after an unlocking movement being imparted to the first of the spring-biased actuators of the clasp assembly.
Figure 4C:
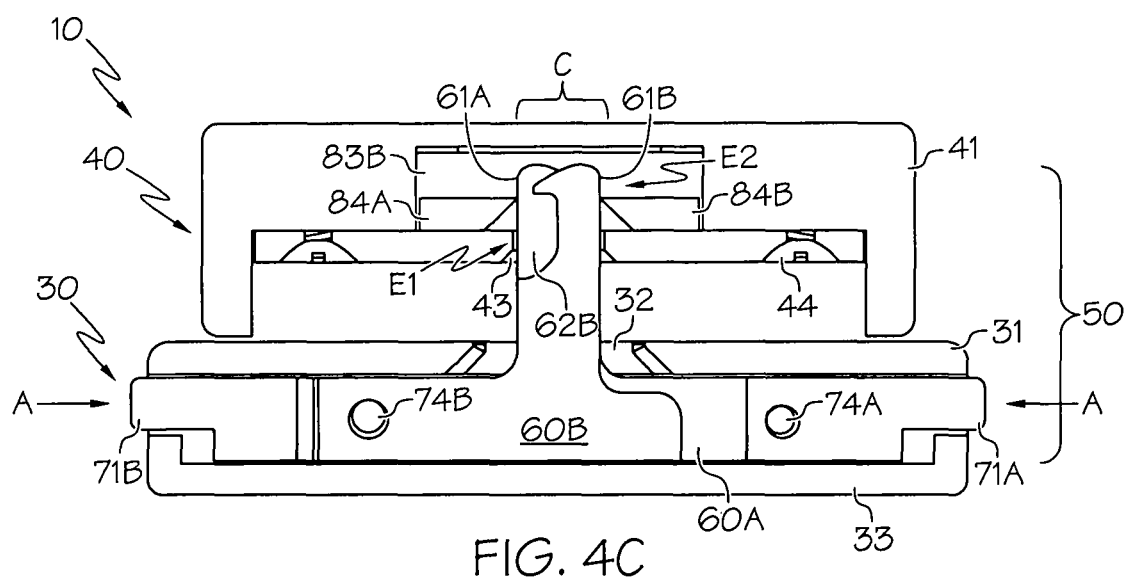
FIG. 4C depicts an elevation cutaway view of the position of the lock arms after an unlocking movement being imparted to both of the first and second spring-biased actuators of the clasp assembly.

Referring next to FIGS. 4A through 4C, internal cutaway views showing the selective locking relationship between the clasp assembly 50 and the corresponding engaging surfaces within the lower and upper housing assemblies 30, 40 are shown. Referring with particularity to FIG. 4A, when the wristband locking mechanism 10 is in the locked position, the lock arms 60A, 60B that are cooperative with the first and second spring-biased actuators 70, 80 exhibit a minimum amount of overlap along the actuation axis A, as evidenced by the relatively small visual obscuring (as viewed in the present figure) of the rearward lock arm 60A by the forward lock arm 60B. In other words, each of the lock arms 60A, 60B are biased in an outward direction consistent with the amount of projection of their respective release buttons 71A, 71A relative to the lower housing 30; such projection ensures that the distal tips 61A, 61B and associated undercut regions 62A, 62B of the lock arms 60A, 60B are pushed as far apart from one another as possible along the actuation axis A Likewise, the sliders 84A, 84B that are part of the second spring-biased actuator 80 are biased in an inward direction such that they extend as far into the undercut region 62A, 62B as possible. As with the aperture 32 that is formed in cover 31 of the lower housing assembly 30, the size and shape of the aperture 43 that is formed in cover 41 is such that edge $E_1$ abuts a portion of the lock arms 60A, 60B such that it acts as a stop for outward movement of the lock arms 60A, 60B along the actuation axis A, thereby defining a maximum travel path along such axis not just for the lock arms 60A, 60B themselves, but also the rigidly-affixed release buttons 71A, 71B of the first spring-biased actuator 70. This use of the movable lock arms 60A, 60B cooperating redundantly with the stationary edge $E_1$ in conjunction with the movable edge $E_2$ ensures that two independent unlocking operations must be undertaken through the use of two independent spring-biased actuators 70, 80 in order to produce the type of interdependent movement needed to free the lock arms 60A, 60B from their interference fit with one or more edges $E_1$, $E_2$. Thus, in one form, the wristband locking mechanism 10 is configured such that in a locking position, the interference fit I is formed between the lock arm pair 60 and edges $E_1$, $E_2$ one of which ($E_1$) is formed directly on a part of the upper housing assembly 40 and the other of which ($E_2$) is formed indirectly on the upper housing assembly 40 through the second spring-biased actuator 80. This interference fit I is selective in that it can be removed by overcoming the spring-biased position of the lock arm pair 60 relative to the edges $E_1$, $E_2$ through the unlocking operations associated with the simultaneous movements of the opposing release buttons 71A, 71B of the first spring-biased actuator 70 in conjunction with the simultaneous movements of the opposing release buttons 81A, 81B of the second spring-biased actuator 80.

Within the present context, the interference fit I that exists between the lock arms 60A, 60B and the edge $E_1$ defined by the aperture 43 of the upper housing assembly 40 or between the lock arms 60A, 60B and the edge $E_2$ defined by the sliders 84A, 84B of the second spring-biased actuator 80 is selective in nature by virtue of its lack of permanence through the user-initiated movement of one member (such as the release buttons 71A, 71B in the first spring-biased actuator 70 and the release buttons 81A, 81B in the second spring-biased actuator 80) to cause a responsive movement of another member (such as the lock arms 60A, 60B or sliders 84A, 84B) in order to overcome an overhanging, overlapping or related relative position that is causing such interference. Also within the present context, the term "simultaneous" when used in conjunction with movement or related engagement of the first and second spring-biased actuators 70, 80 means that both the first and second spring-biased actuators 70, 80 are engaged by a user for a long enough common amount of time to allow both the lock arms 60A, 60B and the sliders 84A, 84B to be moved an amount sufficient to overcome the spring bias and disengage from the interference fit that in turn allows the upper housing assembly 40 to be pivotally moved away from the lower housing assembly 30. Within the present context, this does not necessitate that movement of the first and second spring-biased actuators 70, 80 must take place at the same time, but rather that there is an overlap in time in which both are engaged by the user. As such, movement of one or the other of the first and second spring-biased actuators 70, 80 may be initiated before the other, so long as an amount of time sufficient to permit removal of the interference fit I and subsequent release of the upper housing assembly 40 from the lower housing assembly 30 by the clasp assembly 50 is present. Referring with particularity to FIG. 4B, after release buttons 71A, 71B in the first spring-biased actuator 70 have been engaged, but prior to engagement of the release buttons 81A, 81B in the second spring-biased actuator 80, the undercut regions 62A, 62B of the lock arms 60A, 60B move closer together (that is to say, increase the amount of overlap along the actuation axis A), but are prevented from disengaging the aperture 43 of the upper housing assembly 40 because the spring force present in the second spring-biased actuator 80 forces sliders 84A, 84B (as well as their corresponding edges $E_2$) closer together such that they fit more securely within the undercut regions 62A, 62B. Referring with particularity to FIG. 4C, once the unlocking operation has been completed, there is enough room (indicated by clearance C) to ensure that the clasp assembly 50 in general and the lock arm pair 60 in particular no longer experiences an interference fit with any of the edges $E_1$, $E_2$. Also within the present context, at least some of the interference fits may include a direct fit, such as between a lock arm pair 60 and a corresponding spring-biased actuator 80 such that there is no intervening structure.

Figure 5A:
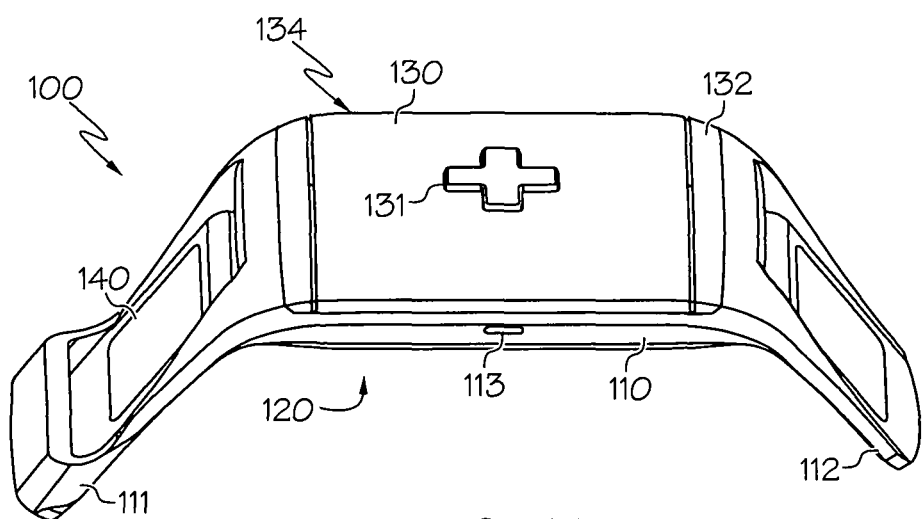
FIG. 5A depicts an upper perspective view of a wearable electronic device that can be secured to a wearer's wrist with the wristband locking mechanism of FIG. 1A.
Figure 5B:
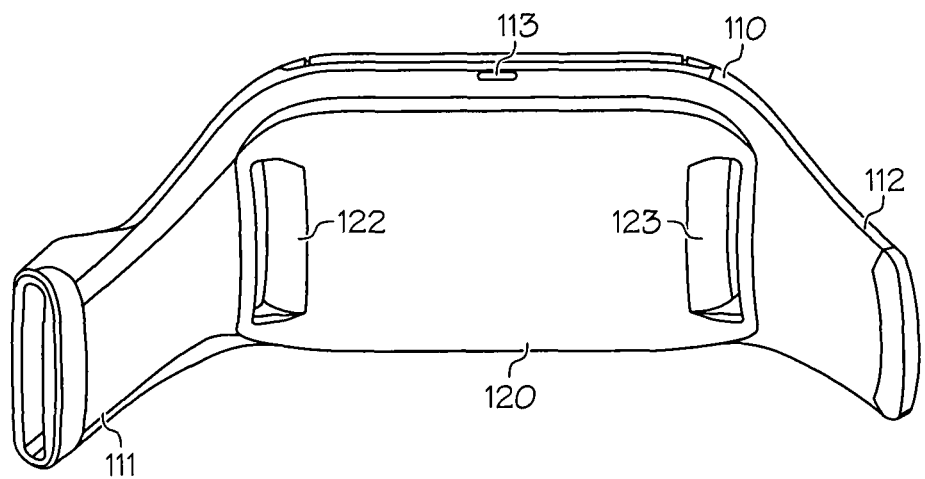
FIG. 5B depicts a lower perspective view of the wearable electronic device of FIG. 5A.
Figure 5C:
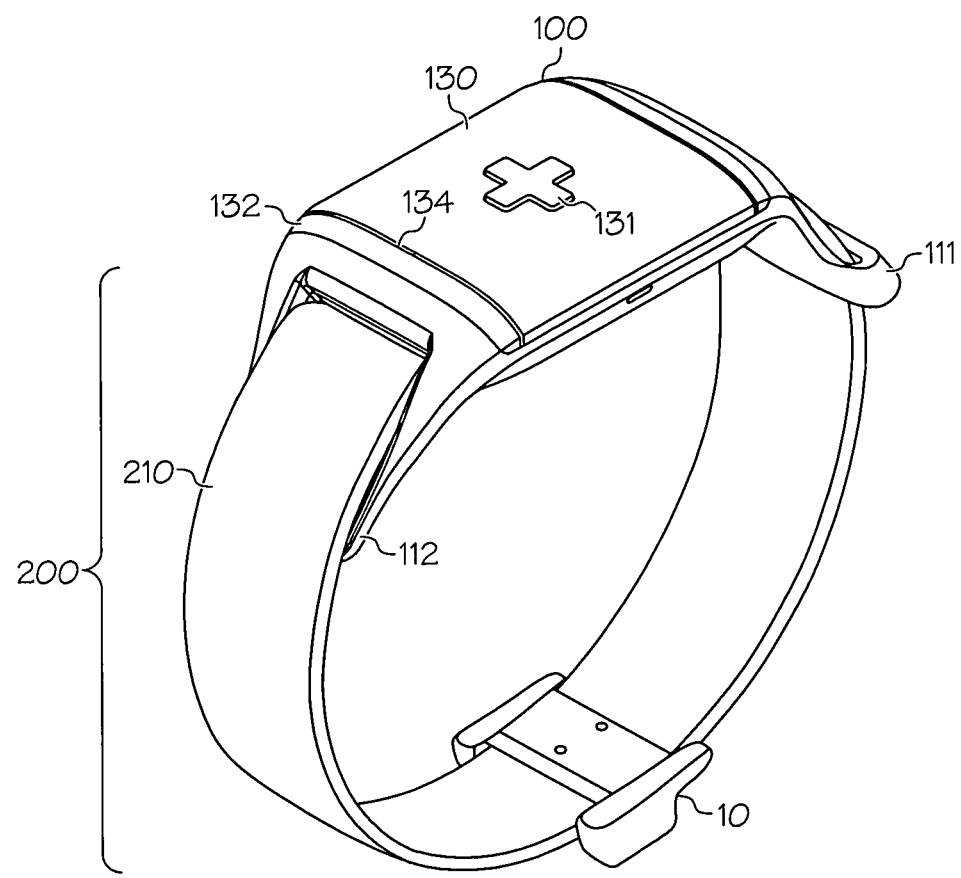
FIG. 5C depicts an upper perspective view of the wearable electronic device of FIG. 5A with a wristband and the wristband locking mechanism of FIG. 1A.

Referring next to FIGS. 5A through 5C, one form of a wearable electronic device that may be used in conjunction with the wristband 200 and locking mechanism 10 is shown. In one form, the wearable electronic device may be configured as a location-tracking device such as that disclosed in U.S. Pat. No. 10,168,430 to Sobol the details of which are incorporated herein by reference in their entirety. Such a location-tracking device may be used with individuals that may have a propensity for wandering, such as those suffering from Alzheimer's Disease, dementia or other cognitive frailties. In another form, the wearable electronic device may be configured as a wellness-monitoring device 100 that may—in addition to having location-tracking attributes—be able to monitor one or more of physiological data, activity data and environmental data as well as to use various communication protocols with which to receive and send such data as a way to gain further insight into one or more indicators of the health of the person wearing the wearable electronic device. In this latter form, the details of the wellness-monitoring device 100 of FIGS. 5A through 5C are disclosed in co-pending U.S. patent application Ser. No. 16/233,462 that is assigned to the assignee of the present disclosure and entitled WEARABLE ELECTRONIC DEVICE AND SYSTEM FOR TRACKING LOCATION AND IDENTIFYING CHANGES IN SALIENT INDICATORS OF PATIENT HEALTH that was filed on Dec. 27, 2018 the contents of which are hereby incorporated by reference.

In either form, the elongate strap 210 that forms the part of the wristband 200 that is wrapped around a wearer's wrist W is deemed to be secured the housing assembly 20 through slidable or fixed connections between the strap 210 and one or more parts of the wristband locking mechanism 10, such as in the slot or gap G that is formed between the dowel pins 90 and the lower housing assembly 30, or in a manner similar to that discussed in conjunction with FIG. 5B. Within the present context, the term "wristband" is meant to includes those used to secure and maintain a watch, smart-watch or the wearable electronic devices disclosed herein, as well as those that serve merely ornamental or decorative functions, such as a bracelet or the like.

Referring with particularity to FIGS. 5A and 5B, the wearable electronic device includes a main housing assembly made up of a housing 110 and a support tray 120. When these two components are joined together, such as by a snap-fit connection, gluing, friction fit or the like, a cavity that is formed in the support tray 120 provides a volumetric space for the mounting of the various electrical and structural components consistent with the construction and operation of the wellness-monitoring device 100 as described in the previously-mentioned and co-pending U.S. patent application Ser. No. 16/233,462. The housing 110 includes a central body, as well as two opposing lateral extensions 111, 112. As will be discussed in more detail below, these lateral extensions 111, 112—in addition to providing a mounting location for a strap or related wristband 200 a conventional NATO-style of which is shown in FIG. 5C—form places where antennae 140 and associated circuitry may be mounted or otherwise encased. Formed in a side edge of the body of the housing 110 is a slot 113 that can be used to allow a fingernail or small sharp object to be inserted as a way to unlock the housing 110 from a top plate 130. Referring with more particularity to FIG. 5B, the lower perspective view shows how an elongated strap 210 that which makes up a part of the wristband 200 may be affixed to the wellness-monitoring device 100. In particular, the housing 110 and its support tray 120 may be configured to define a hollow region between them a part of which is shown by openings 122, 123 in FIG. 5B such that the elongated strap 210 may be inserted.

As discussed in the previously-mentioned and co-pending U.S. patent application Ser. No. 16/233,462, numerous sensors S may be advantageously located inside the wellness-monitoring device 100. For example, some sensors S (shown generally as being embedded in support tray 120, but understood to be placed anywhere in or on the wellness-monitoring device 100 in such a manner as to facilitate acquiring data that in turn may be used by an algorithm (including machine learning and clinical decision support variants) to provide indicia of environmental, activity or physiological traits associated the wearer of the wellness-monitoring device 100. In one form, the sensors S may act in conjunction with one another—as well as with instructions that are stored on a machine-readable medium—to aggregate (or fuse) the acquired data in order to infer certain activities, conditions or circumstances. In one form, such data fusion (also referred to as sensor fusion) may take advantage of acquired audio information (such as from microphones that can detect door closings, toilet flushings, turning on faucets or the like), movement information (such as from gravity-measuring accelerometers, inertial measurement units (IMUs), magnetic field-measuring magnetometers, gyroscopes or motion detectors that can record movement, including falls, high or low gait speed or the like). Such sensor fusion can significantly improve the operability of the wellness-monitoring device 100 by leveraging the strengths of each sensor to provide more accurate values of the acquired data. For example, gyroscopic measurement alone can lead to accumulating errors, while the absolute reference of orientation associated with accelerometers and magnetometers may be prone to high noise levels. By fusing the acquired data, the sensors S and accompanying data-processing instructions can filter the information in order to compute a single estimate of (six degree-of-freedom) movement, orientation or position, which in turn simplifies downstream computational requirements. In one form, the sensors S are non-invasive in that they need not be ingested or in percutaneous, subcutaneous or intravenous form. Sensors S may be configured to acquire various forms of activity, environmental and physiological data; such data may then be filtered, amplified and converted (such as by an A/D converter), either onboard the wellness-monitoring device 100 or remotely (such as on one or more servers), in either event via local processor, memory and executable instructions.

As seen with particularity in FIGS. 5A and 5B, in one form, the top plate 130 includes a nurse call button 131 formed on an upper surface thereof. In addition, at least a pair of opposing lateral edges 132 of the top plate 130 may be made from a transparent or translucent material such that a light-emitting diode (LED) source that may be formed underneath can be made to pass through the opposing lateral edges 132 in order to have an outward-illuminating effect. In one form, light pipes may convey the light from the LED source to the opposing lateral edges 132. Although the top plate 130 is shown with an activatable nurse call button 131, it will be appreciated that the wellness-monitoring device 100 may be configured with different top plates 130. Such variants may include a frame-like top cover that can contain a family picture, a fidget plate or other features. For configurations where the nurse call button 131 is an active device, in one form, a small magnet may be included as part of the circuitry to have a capacitance sensor. Thus, when the nurse call button 131 is activated, the electronics in the wellness-monitoring device 100 detects the presence of the magnet in the plate 130 and enables the nurse call button 131. In such a configuration, a light source such as a thin LED band 134 may be illuminated to let the patient know that the nurse call button 131 is being activated. Likewise, in a configuration where the nurse call button 131 feature is not installed, there is no magnet that is sensed and the wellness-monitoring device 100 automatically disables the nurse call feature.

In configurations where the nurse call button 131 is installed, when the user presses it, a signal may be sent to a remote backhaul (such as the cloud, an application server, network server or the like) via hybrid communication module such as that discussed in the previously-mentioned and co-pending U.S. patent application Ser. No. 16/233,462 to indicate that the user needs help. In response, the backhaul sends notifications to facility staff (nurses, aides, management or the like) informing them that a person to whom the wellness-monitoring device 100 is attached is in need of assistance. When a staff member or other caregiver reaches the person, they can clear the call by depressing the nurse call button 131. When the nurse call button 131 is pressed again, the hybrid communication module searches for a nearby BLE signal from a tag or related beacon that is being worn by the staff member. The code from the tag identifies the staff member and this code is sent to the application server to be logged. This way, the system 1 keeps track of when a person calls for help, how long it took for help to arrive, and who from the staff provided the help to the person.

In addition to having a BLE radio receiver in the form of multiple wireless communication sub-modules, the hybrid communication module of the wellness-monitoring device 100 may act as a GNSS receiver. The wellness-monitoring device 100 may also transmit events to the BLE beacon or a gateway device via LPWAN, such as that being transmitted under a protocol that is governed by the LoRa Alliance. In one form, LPWAN is primarily used as an uplink-based network such that the wellness-monitoring device 100 is acting as an end-node that initiates the LPWAN communication with yet another wireless communication sub-module of the hybrid communication module. Unlike relying upon BLE to transmit the collected location, activity, environmental and physiological data, where numerous BLE hubs would have to be deployed (often in a mesh topology) in order to ensure signal reception over the entirety of an assisted living community facility, the LPWAN-based approach disclosed herein allows coverage of the entire facility with a smaller number of gateways in a star topology such that a wireless network formed between the wellness-monitoring device 100 and the gateway has sufficient redundancy to ensure that data signals being transmitted from the wellness-monitoring device 100 arrive at the backhaul server, regardless of the failure of a single gateway. Significantly, using a single gateway (or no more than a small number for very large facilities and system deployments) can reach the backhaul server with minimum amount of installation time and expense, as well as no (or limited) need to integrate into existing WiFi infrastructure that may already be present within the facility. Gateways transfer a received packet from the wellness-monitoring device 100 to the cloud-based network server via some additional backhaul (such as cellular, ethernet, satellite or Wi-Fi). In one form, the backhaul may be used to eliminate duplicate packets, schedule acknowledgements, adapt data rates and provide encrypted communication with the wellness-monitoring device 100, as well as other devices.

In one form, a status indicator may be included to provide an indication of the locking status of the locking mechanism 10. Such status indicator may also include an alert if the locking mechanism 10 is not in a locked (that is to say, secured) position, or becomes unlocked once already secured to a wearer. In one form, the status indicator may include its own circuit that is signally cooperative with the processor or one or more contacts, switches or related sensors to detect (such as through a closed versus open connection) whether the wristband locking mechanism is in the locked position or the unlocked position. Such a status indicator may include one or more of audible, visual and haptic devices in order to convey such an alert to the wearer and the immediately adjacent surroundings. In addition, the status indicator may be placed—such as through the processor, memory and related circuitry—into signal communication with the hybrid communication module 175 to convey a message to one or more of the wellness-monitoring device 100 (in situations where the status indicator circuitry does not form a part of the circuitry of the wellness-monitoring device 100), backhaul or third-party monitor the latter of which may be a nurse, caregiver or other interested party through a downloadable application onto a mobile telephone, tablet, computer or other such device equipped with one or more telecommunications protocols.

In another form, an article or device being secured to a wearer by the locking mechanism 10 need not be the location-tracking device or wellness-monitoring device 100 as depicted in FIG. 5C, but can be any other device or item designed to be worn by, affixed to or otherwise secured to a wearer. Such other articles or devices may include jewelry, a wristwatch, an article of clothing, an elongate strap or the like, and the use of the locking mechanism 10 as disclosed herein in conjunction with all such other articles or devices is deemed to be within the scope of the present disclosure.

Figure 6:
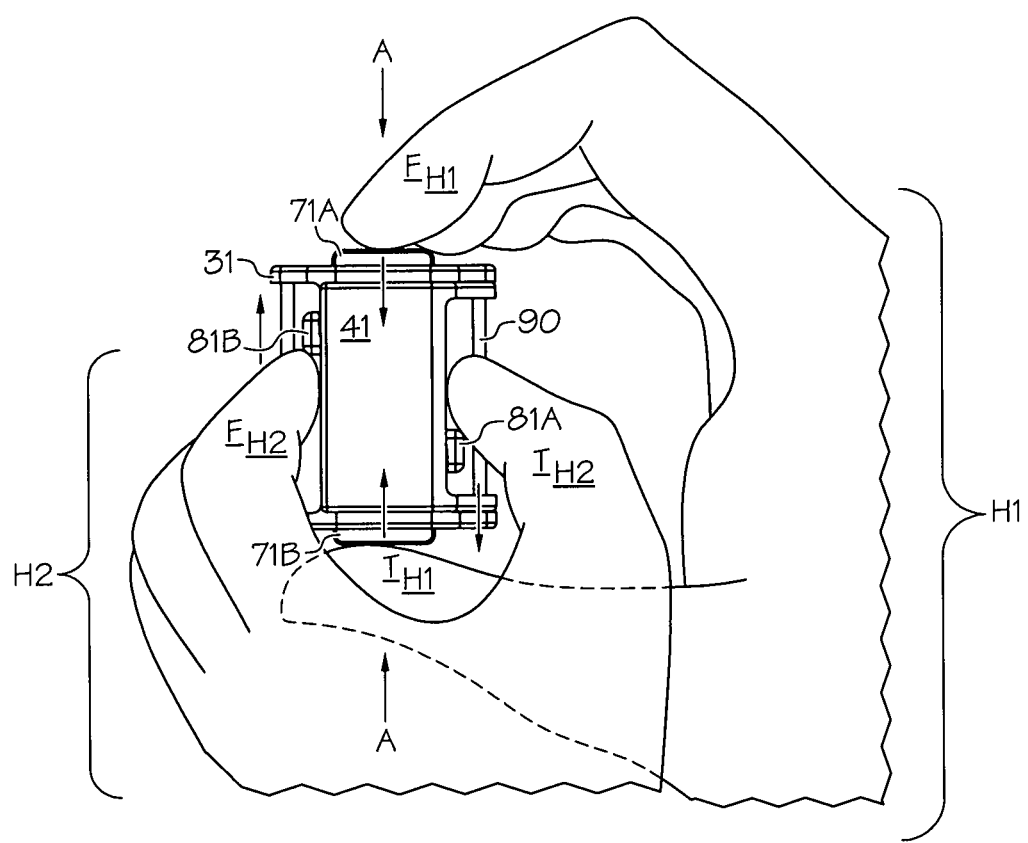
FIG. 6 depicts a top view of the wristband locking mechanism of FIG. 1A, along with notional finger grasping and arrow movement for the two-handed unlocking sequence of FIGS. 4A through 4C.

Referring next to FIG. 6 in conjunction with FIGS. 7A and 7B, details of unlocking the wristband locking mechanism 10 are shown. Referring first to FIG. 6, a top view of the wristband locking mechanism 10 is shown to indicate how two-handed operation is used to simultaneously move the two sets of release buttons 71A, 71B and 81A, 81B that in turn cause the release of the upper housing assembly 40 from the lower housing assembly 30 through clasp assembly 50. As can be seen, when moved, such as through a longitudinally-directed splaying force imparted by a user's thumb $T_{H2}$ and forefinger $F_{H2}$ on a second hand $H_2$, the release buttons 81A, 81B of the second spring-biased actuator 80 are displaced in the direction shown along the actuation axis A. As can be seen from FIGS. 4A through 4C and the contact of edges $E_1$, $E_2$ against their respective parts of the undercut regions 62A, 62B of the lock arms 60A, 60B, while the first and second spring-biased actuators 70 and 80 of the clasp assembly 50 can be actuated independently of one another, it is only through their redundancy of simultaneous actuation that the interdependent unlocking movement of the wristband locking mechanism 10 takes place. As such, the wristband locking mechanism 10 avoids one-handed unlocking by the wearer of the wristband 200. In another form (not shown), the longitudinally-directed splaying force imparted by the user's thumb $T_{H2}$ and forefinger $F_{H2}$ on the second hand $H_2$ could be replaced by a compressive force on the release buttons 81A, 81B by the same fingers. It will be appreciated that in such an alternate form, various other components of the second spring-biased actuator 80 (most notably the springs 82A, 82B) would have to be rearranged to effect an opposing bias to the one depicted in FIGS. 3B through 3D in order to ensure proper operability associated with the unlocking operation. Nevertheless, the authors of the present disclosure are of the belief that using a splaying rather than compressive movement on the release buttons 81A, 81B in conjunction with the independent unlocking operations of two spaced-apart release buttons 71A, 71B of the first spring-biased actuator 70, the opposing movements of the thumb $T_{H1}$ and forefinger $F_{H1}$ of the first hand $H_1$ from those of the second hand $H_2$ makes it more difficult for a wearer of a corresponding wristband or wearable electronic device to undesirably remove it by himself or herself. While the present disclosure refers to the various unlocking operations within the context of thumbs and forefingers, it will be appreciated that other finger combinations may be used including the middle finger, ring finger or little finger, and that all such variants are deemed to be within the scope of the present disclosure.

Referring with particularity to FIGS. 7A and 7B in conjunction with FIGS. 3B through 3D and 4A through 4C, a portion of the sequence used to attach a wristband 200 and housing 110 of FIG. 5C is shown. Unlike the unlocking operation discussed elsewhere in this disclosure, where a coordinated effort between the first and second spring-biased actuators 70 and 80 is required to unlock the locking mechanism 10, the cooperation between the inclined planes 85A, 85B of the corresponding sliders 84A, 84B is shaped to improve movement response. Thus, upon a closing force used to hingedly bring the upper housing assembly 40 into registration with the lower housing assembly 30, the distal tips 61A, 61B of the lock arms 60A, 60B cause contact with the angled surface of the inclined planes 85A, 85B which—due to their restricted movement within the upper housing assembly 40 only along the actuation axis A—causes the sliders 84A, 84B to overcome the bias in springs 82A, 82B until such movement produces a clicking sound or related indicia of the return of the redundant interference fit I between the undercut region 62A, 62B of the lock arms 60A, 60B and the edge $E_1$ formed by the aperture 43 of the upper housing assembly 40, as well as between the undercut region 62A, 62B of the lock arms 60A, 60B and the edge $E_2$ of the sliders 84A, 84B. In one form, such closing force can be to snap the upper housing assembly 40 shut onto the lower housing assembly 30.

Within the present disclosure, the term "patient" is meant to include a person who is either under short-term or long-term in-patient or out-patient care of a doctor, nurse or other professional caregiver within a hospital or doctor's office, as well as a person who either resides at home under a home health-care model, or is a resident either at home or within an assisted living model or related long-term or short-term care model regardless of whether such person is or is not under the present care of a doctor, nurse or other professional caregiver. Accordingly, the various terms used herein to identify the wearer of the locking mechanism 10 as a "patient", "user", "individual" or "person" are deemed to be equivalents within the present disclosure, and that any greater degree of specificity as required of such terms will be apparent from the context.

Within the present disclosure, the use of the prepositional phrase "at least one of" is deemed to be an open-ended expression that has both conjunctive and disjunctive attributes. For example, a claim that states "at least one of A, B and C" (where A, B and C are definite or indefinite articles that are the referents of the prepositional phrase) means A alone, B alone, C alone, A and B together, A and C together, B and C together, or A, B and C together. By way of example within the present context, if a claim recites that a processor acquires at least one of environmental data, activity data and physiological data from at least one of a plurality of sensors, and if such data is environmental data alone, activity data alone, physiological data alone or any combination of such environmental, activity and physiological data, then such data acquisition satisfies the claim.

Within the present disclosure, the following claims are not written in means-plus-function format and are not intended to be interpreted based on 35 USC 112(f) unless and until such claim limitations expressly use the phrase "means for" followed by a statement of function void of further structure.

It is noted that one or more of the following claims utilize the term "wherein" as a transitional phrase. For the purposes of defining features discussed in the present disclosure, it is noted that this term is introduced in the claims as an open-ended transitional phrase that is used to introduce a recitation of a series of characteristics of the structure and should be interpreted in like manner as the more commonly used open-ended preamble term "comprising."

It is noted that terms like "preferably", "generally" and "typically" are not utilized in the present disclosure to limit the scope of the claims or to imply that certain features are critical, essential, or even important to the disclosed structures or functions. Rather, these terms are merely intended to highlight alternative or additional features that may or may not be utilized in a particular embodiment of the disclosed subject matter. Likewise, it is noted that the terms "substantially" and "approximately" and their variants are utilized to represent the inherent degree of uncertainty that may be attributed to any quantitative comparison, value, measurement or other representation. As such, use of these terms represents the degree by which a quantitative representation may vary from a stated reference without resulting in a change in the basic function of the subject matter at issue.

It will be apparent to those skilled in the art that various modifications and variations can be made to the described embodiments without departing from the spirit and scope of the claimed subject matter. Thus it is intended that the specification cover the modifications and variations of the various described embodiments provided such modification and variations come within the scope of the appended claims and their equivalents.

Having described the subject matter of the present disclosure in detail and by reference to specific embodiments, it is noted that the various details disclosed in the present disclosure should not be taken to imply that these details relate to elements that are essential components of the various described embodiments, even in cases where a particular element is illustrated in each of the drawings that accompany the present description. Further, it will be apparent that modifications and variations are possible without departing from the scope of the present disclosure, including, but not limited to, embodiments defined in the appended claims. More specifically, although some aspects of the present disclosure may be identified as preferred or particularly advantageous, it is contemplated that the present disclosure is not necessarily limited to these aspects.

What is claimed is:

1. A wristband locking mechanism comprising:
a housing assembly; and
a clasp assembly cooperative with the housing assembly, the clasp assembly comprising;
  a lock arm pair;
  a first spring-biased actuator cooperative with the lock arm pair to provide a first selective interference fit between the lock arm pair and a portion of the housing assembly; and
  a second spring-biased actuator cooperative with the lock arm pair to provide a second selective interference fit between the lock arm pair and a portion of the housing assembly, wherein a state of the wristband locking mechanism is changed upon the first and second spring-based actuators being simultaneously engaged through two-handed user actuation.

2. The wristband locking mechanism of claim 1, wherein the housing assembly comprises a lower housing assembly movably coupled to an upper housing assembly.

3. The wristband locking mechanism of claim 2, wherein the lower housing assembly is hingedly coupled to an upper housing assembly.

4. The wristband locking mechanism of claim 3, wherein the first spring-biased actuator is secured within the lower housing assembly and the second spring-biased actuator is secured within the upper housing assembly.

5. The wristband locking mechanism of claim 4, wherein (i) the first selective interference fit is between a lock arm of the first spring-biased actuator and an edge formed on the second spring-biased actuator, and (ii) the second selective interference fit is between a lock arm of the second spring-biased actuator and an edge formed on the upper housing assembly.

6. The wristband locking mechanism of claim 3, wherein upon the two-handed user actuation, movement of the first and second spring-biased actuators takes place along a common axial dimension.

7. The wristband locking mechanism of claim 6, wherein the selective interference fit is (i) between the lock arm pair and a first edge formed directly on the upper housing assembly, and (ii) between the lock arm pair and a second edge formed indirectly on the upper housing assembly.

8. The wristband locking mechanism of claim 7, wherein the second edge is formed on a movable part of the second spring-biased actuator.

9. The wristband locking mechanism of claim 1, wherein the second interference fit comprises a direct fit between the lock arm pair and the second spring-biased actuator.

10. The wristband locking mechanism of claim 1, wherein the changed state comprises either from a locked position to an unlocked position upon the first and second spring-based actuators being simultaneously engaged through two-handed user actuation or from an unlocked position to a locked position upon the first and second spring-based actuators being simultaneously engaged through two-handed user actuation.

11. A method of securing an article to a person, the method comprising:
 coupling a locking mechanism to the article;
 attaching the article to the person; and
 locking the locking mechanism, wherein the locking mechanism comprises:
  a housing assembly; and
  a clasp assembly cooperative with the housing assembly, the clasp assembly comprising;
   a lock arm pair;
   a first spring-biased actuator cooperative with the lock arm pair to provide a first selective interference fit between the lock arm pair and a portion of the housing assembly; and
   a second spring-biased actuator cooperative with the lock arm pair to provide a second selective interference fit between the lock arm pair and a portion of the housing assembly, wherein a state of the locking mechanism is changed upon the first and second spring-based actuators being simultaneously engaged through two-handed user actuation.

12. The method of claim 11, wherein the article comprises a wristwatch.

13. The method of claim 11, wherein the article comprises an article of clothing.

14. The method of claim 11, wherein the article comprises at least one piece of jewelry.

15. The method of claim 11, wherein the article comprises wearable electronic device.

16. The method of claim 15, wherein the wearable electronic device comprises a person tracking device.

17. The method of claim 15, wherein the wearable electronic device comprises a person wellness-monitoring device.

* * * * *